United States Patent [19]

Huynh et al.

[11] Patent Number: 5,750,722
[45] Date of Patent: May 12, 1998

[54] METHOD FOR THE PREPARATION OF HIGH PURITY SUBSTITUTED BENZ [E] INDOLES AND THE ALKALINE SALTS THEREOF

[75] Inventors: Anh Hoa Huynh, Paris; Joanne Tran, Argenteuil; François Scherninski; Jean-Paul Guette, both of Paris, all of France

[73] Assignee: Societe D'etudes et de Recherches Biologiques, Paris, France

[21] Appl. No.: 617,897

[22] PCT Filed: Sep. 14, 1994

[86] PCT No.: PCT/FR94/01077

§ 371 Date: Jun. 11, 1996

§ 102(e) Date: Jun. 11, 1996

[87] PCT Pub. No.: WO95/07888

PCT Pub. Date: Mar. 23, 1995

[30] Foreign Application Priority Data

Sep. 17, 1993 [FR] France ................... 93 11121

[51] Int. Cl.$^6$ .............. C07D 209/56; A61K 49/00; A61K 31/40
[52] U.S. Cl. .............. 548/427; 424/9.1; 514/411
[58] Field of Search ............ 548/427; 424/9.1; 514/411

[56] References Cited

U.S. PATENT DOCUMENTS

| | | |
|---|---|---|
| 2,251,286 | 8/1941 | Keyes .................. 548/427 X |
| 2,895,955 | 7/1959 | Hesbltine et al. ........ 548/427 X |
| 3,845,073 | 10/1974 | Newberry .............. 548/427 |
| 4,370,341 | 1/1983 | Asselin et al. ........... 424/274 |

FOREIGN PATENT DOCUMENTS 2046141  3/1972  Germany ................ 548/427

OTHER PUBLICATIONS

Arakawa et al, Chemical Abstracts, vol. 114, #175012e (1991).
Ata et al, Chemical Abstracts, vol. 116, #162619z (1992).
The Merck Index, 11th Edition, p. 1158 (1988).

Primary Examiner—Floyd D. Higel
Attorney, Agent, or Firm—Evenson, McKeown, Edwards & Lenahan, P.L.L.C.

[57] ABSTRACT

Method for the preparation of high purity substituted benz[e]indoles corresponding to the general formula

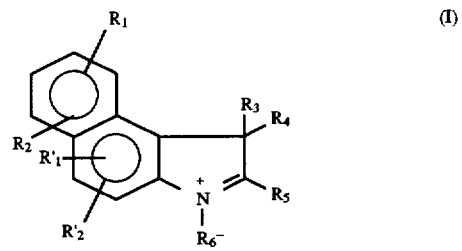

(I)

comprising the preparation of an arylhydrazine which is subjected to a Fischer indole synthesis with a suitable ketone, the benz[e]indole thus obtained being reacted with a radical $R_6$, followed by subjection to a purification step.

This method may more particularly be applied to the synthesis of Indocyanine Green.

9 Claims, No Drawings

METHOD FOR THE PREPARATION OF HIGH PURITY SUBSTITUTED BENZ [E] INDOLES AND THE ALKALINE SALTS THEREOF

This application is a 371 of PCT/FR94/01077 filed Sep. 14, 1994.

The subject of the invention is a method for the preparation of high purity substituted benz[e]indoles corresponding to the general formula

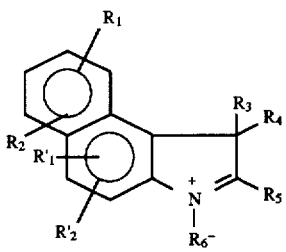

in which $R_1$, $R_2$, $R'_1$, $R'_2$, $R_3$, $R_4$ and $R_5$, which are identical to or different from each other, represent hydrogen atoms, $C_1$ to $C_{12}$ alkyl groups, $C_1$ to $C_4$ sulphoalkyl, cycloalkyl or alkoxyl groups, aryl or aroxyl groups, or halogen atoms, and $R_6$ represents a $C_1$ to $C_7$, preferably $C_1$ to $C_4$, sulphoalkyl, haloalkyl or hydroxycarbonylalkyl group, it being also possible for $R_5$ to represent a group of formula

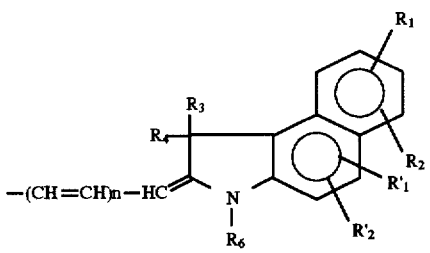

in which n represents an integer from 1 to 7.

It also relates to the preparation of the alkaline salts of the substituted benz[e]indoles of formula (I).

Its subject more particularly is the application of the abovesaid method to the preparation of Indocyanine Green or the internal salt, i.e. sodium salt of 2-{7-[1,3-dihydro-1, 1-dimethyl-3-(4-sulphobutyl)-2H-benz[e]indol-2-ylidene]-1,3,5-heptatrienyl}-1,1-dimethyl-3-(4-sulpho-butyl)-1H-benz[e]indolium hydroxide represented by the formula:

The substituted benz[e]indoles of formula (I) are most often dyes which are used especially in industry.

Thus, Indocyanine Green is a dye essentially intended for the photographic industry.

It has also been proposed to make use of Indocyanine Green as a dye in the pharmaceutical industry, especially as a diagnostic aid, in particular for determining the volume of blood, the heart pump rate and for controlling the functioning of the liver.

Now, the reason for which Indocyanine Green has never been truly able to establish itself as a dye in the pharmaceutical industry field is due to the fact that the known processes for the preparation of the benz[e]indoles of formula (I) in general and of Indocyanine Green in particular lead to products for which it is impossible, in practical terms, to arrive at a sufficient degree of purity to avoid all allergenic, or even toxic, phenomena.

Indeed, the products of the type in question which are already found on the market exhibit, because of their preparation process, in particular a residual content of iodide ions which it is impossible to bring, under acceptable economic conditions, to a sufficiently low level to avoid any toxic phenomena.

It has, indeed, been proposed to avoid the use of iodine in the preparation of the products of the type in question, but it is found that the approaches envisaged employ toxic solvents, in particular methanol.

Furthermore, the known processes employ carcinogenic amines, in particular β-naphthylamine.

Thus, the aim of the invention is especially to provide a process for the preparation of the substituted benz[e]indoles of formula (I), and in particular of Indocyanine Green, which no longer has the disadvantages of the processes of the prior art and which consequently leads to products of high purity which are substantially free of iodide ions, traces of carcinogenic amines and toxic solvents.

The Applicant Company has, to its credit, developed a process allowing this aim to be achieved and which is characterized in that the following are successively performed an arylhydrazine of the following formula is prepared:

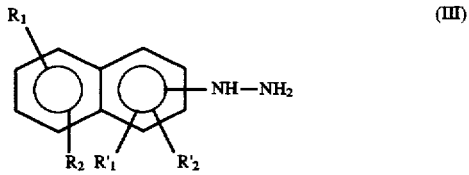

by reaction of hydrazine with the corresponding aryl hydroxyl, thus avoiding any use of carcinogenic amines.

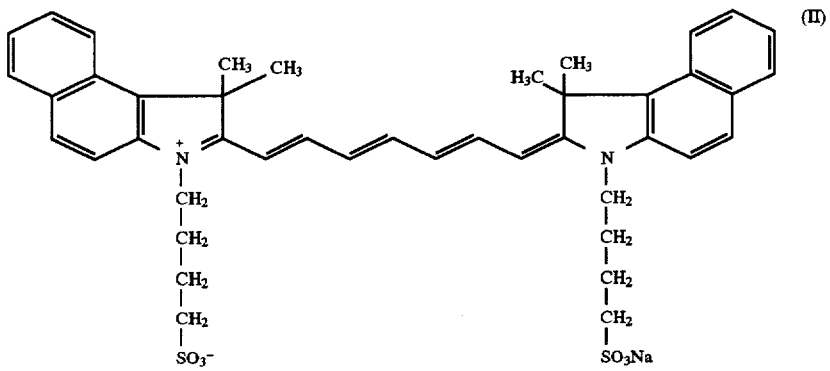

a Fischer indole synthesis is carried out between the arylhydrazine of formula (III) and a ketone of formula:

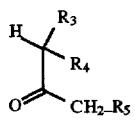

which gives a benz[e]indole of formula:

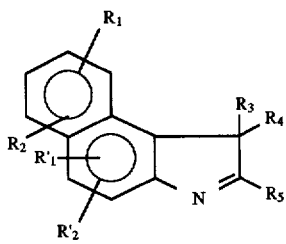

the benz[e]indole of formula (I) is formed by reaction of the benz[e]indole of formula (V) with the radical $R_6$ which represents a $C_1$ to $C_7$, preferably $C_1$ to $C_4$, sulphoalkyl, haloalkyl or hydroxycarbonylalkyl group, the meanings of $R_1$, $R_2$, $R'_1$, $R'_2$, $R_3$, $R_4$ and $R_5$ being those given in relation to the formula (I), the only difference being that $R_5$ cannot represent a group of formula (I'), the benz[e]indole of formula (I) thus prepared is converted, where appropriate, into a soluble alkaline salt by reaction with an alkaline alkoxide or an alkaline salt of an organic acid, in particular with sodium acetate, the benz[e]indole of formula (I) or, if it has been prepared, the corresponding alkaline salt, being freed of its residual impurities, preferably by extraction using an apolar solvent whose boiling point is close to that of acetone, it being possible for this solvent to be chosen from the group comprising in particular pentane, hexane, heptane, cyclohexane and petroleum ether.

According to a particular embodiment of the abovementioned process, the benz[e]indole of formula (I) in which $R_5$ represents the abovementioned group of formula (I'), is prepared by first reacting the sulphonic derivative of the benz[e]indole of formula (I) with glutaconic aldehyde dianilide hydrochloride, followed by reaction of the product thus obtained with a second molecule of the abovementioned sulphonic derivative of the benz[e]indole of formula (I).

According to another advantageous embodiment of the abovementioned process, applied to the synthesis of Indocyanine Green, the following are successively performed the benz[e]indole of formula (V) in which, on the one hand, $R_1$, $R_2$, $R'_1$ and $R'_2$ are hydrogen atoms and, on the other hand, $R_3$, $R_4$ and $R_5$ are methyl radicals, is prepared by reaction of 2-naphthylhydrazine with isopropyl methyl ketone, the benz[e]indole thus obtained is reacted with 1,4-butane-sultone, the resulting product of this reaction is condensed with glutaconic aldehyde dianilide hydrochloride in acetic medium, and the product thus formed is reacted, in an ethanolic medium, with a second molecule of the benz[e]indole of formula (V) containing the same 1,4-butane-sultone radical on the nitrogen atom, conversion into a water-soluble salt being carried out by directly introducing an alkaline alkoxide or an alkaline salt of an organic acid, in particular sodium acetate, into the reaction medium.

The preparation of arylhydrazine is carried out in a hot aqueous medium, in particular at a temperature of approximately 100 to approximately 160° C. and at a pressure of approximately 50 to 150 bar in particular.

It is recalled that the principle of the Fischer indole synthesis is to react an arylhydrazine with a suitably selected ketone in an acidic medium (see for example "The Fischer Indole Synthesis" by B. Robinson, Chem. Rev., vol. 63 (1963), pages 371–401.

The invention will be even better understood with the aid of the non-limiting example which follows and which more particularly relates to the preparation of Indocyanine Green.

EXAMPLE

Preparation of 2-naphthylhydrazine 57.6 g (0.4 mol) of 2-naphthol and 200 ml of hydrazine (4 mol) are introduced into a 500 ml autoclave. The mixture is stirred at 85° C. at a pressure of 60 bar for approximately 100 hours. The reaction medium is subsequently extracted with dichloromethane. The organic phase is washed with 10% sodium hydroxide, then with water and finally with brine; it is dried over magnesium sulphate. After filtration and evaporation under vacuum, 50.6 g (80%) of product are obtained, the melting point of which is 124° C. (alcohol/water).

Preparation of Indocyanine Green in acid form 50 g (0.32 mol) of 2-naphthylhydrazine are reacted with 48 ml (0.45 mol) of isopropyl methyl ketone in an aqueous acetic medium.

46.8 g (70%) of 1,1,2-trimethylbenz[e]indole are thus obtained (melting point 114° C.), to which are added 33 g (0.24 mol) of 1,4-butane-sultone.

After washing with acetone, 68 g (90%) of sulphonic derivative are collected.

34 g of this derivative are reacted with 31 g (0.11 mol) of glutaconic aldehyde dianilide hydrochloride in 170 ml of acetic anhydride with stirring, the temperature being 130° C. The mixture is cooled to room temperature and the stirring is continued for 30 minutes.

A precipitate of anhydro-2-(6-acetanilido-1,3,5-hexatrienyl)-3,3-dimethyl-1-(4-sulphobutyl)-4,5-benzopseudoindolium hydroxide forms, which is washed with acetone and then dried.

The mass of the dried hexatriene product thus obtained is 42.7 g (80%); its melting point is 168°–170° C. (with decomposition).

13.8 g (25.5 mmol) of the latter product are dissolved in 80 ml of anhydrous ethanol and 8.8 g (25.5 mmol) of the sulphonic derivative obtained above are added; after addition of 2.6 g (25.5 mmol) of triethylamine, the mixture is heated at reflux for 15 minutes; after cooling, a precipitate (15.8 g) of Indocyanine Green in an acid form is obtained.

Preparation of Indocyanine Green sodium salt 42.7 g (78.8 mmol) of the abovementioned hexatriene product are dissolved in 250 ml of anhydrous ethanol and 27.3 g (78.8 mmol) of the sulphonic derivative obtained above are added at the same time as 8 g (78.8 mmol) of triethylamine; after cooling, 6.5 g (78.8 mmol) of sodium acetate dissolved beforehand in 450 ml of anhydrous ethanol are added directly into the reaction medium with stirring for 30 minutes.

The salt formed is drained, washed with acetone and dried.

15.8 g (80%) of the desired product are obtained, the melting point of which is 243° C. (with decomposition).

Purification

The abovementioned Indocyanine Green in sodium salt form is purified by extraction of the impurities at reflux, using acetone as solvent.

The product obtained, free of iodide ions, contains less than 0.5% of residual impurities; it is suitable for all applications in the pharmaceutical field and in particular as a dye in infrared angiography.

We claim:

1. Method for preparing a substituted benz[e]indole containing less than 0.5% of residual impurities and corresponding to the formula:

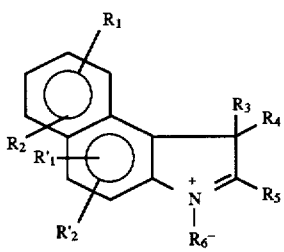

in which $R_1$, $R_2$, $R'_1$, $R'_2$, $R_3$ and $R_4$, which are identical to or different from each other, represent a hydrogen atom, a $C_1$ to $C_{12}$ alkyl group, a $C_1$ to $C_4$ sulphoalkyl, cycloalkyl or alkoxyl group, an aryl or aroxyl group, or a halogen atom, and $R_6$ represents a $C_1$ to $C_7$ sulphoalkyl, haloalkyl or hydroxycarbonylalkyl group, $R_5$ represents a hydrogen atom, a $C_1$ to $C_{12}$ alkyl group, a $C_1$ to $C_4$ sulphoalkyl, cycloalkyl or alkoxyl group, an aryl or aroxyl group, a halogen atom or a group of formula:

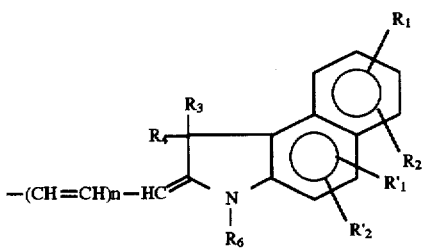

in which n represents an integer from 1 to 7, the said method successively comprising:

preparing an arylhydrazine of the following formula:

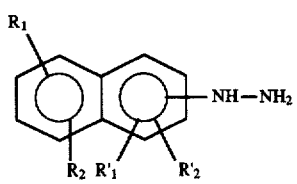

by reacting hydrazine with the corresponding aryl hydroxyl, carrying out a Fischer indole synthesis between the arylhydrazine of formula (III) and a ketone of formula:

to obtain a benz[e]indole of formula:

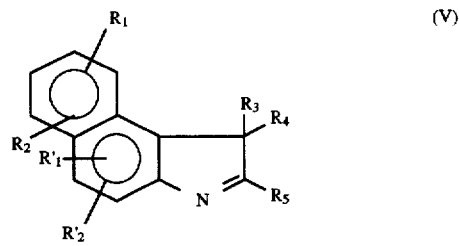

forming the sulphonic derivative of the benz[e]indole of formula (I) by reacting the benz[e]indole of formula (V) with a molecule comprising the radical $R_6$, converting the thus prepared benz[e]indole of formula (I) into a soluble alkaline salt by reaction with an alkaline alkoxide or an alkaline salt of an organic acid, the alkaline salt thus obtained being freed of its residual impurities by extraction using acetone or an apolar solvent whose boiling point is close to that of acetone, with the proviso that when $R_5$ represents the group of formula:

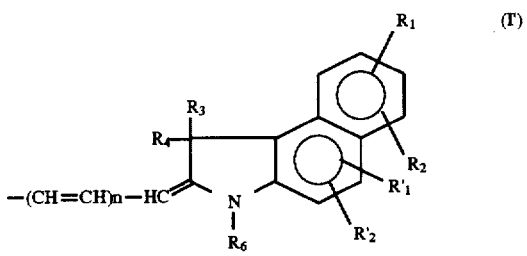

the sulphonic derivative of the benz[e]indole of formula (I) is first reacted with glutaconic aldehyde dianilide hydrochloride, and the product thus obtained is reached with a second molecule of the above-mentioned sulphonic derivative of the benz[e]indole of formula (I).

2. Method according to claim 1, wherein $R_6$ represents a $C_1$ to $C_4$ sulphoalkyl, cycloalkyl or alkoxyl group.

3. Method according to claim 1, wherein the benz[e]indole of formula (I) is converted into a soluble alkaline salt by reaction with sodium acetate.

4. Method according to claim 1, wherein the alkaline salt of the benz[e]indole of formula (I) is freed of its residual impurities by extraction with an apolar solvent selected in the group consisting of pentane, hexane, heptane, cyclohexane and petroleum ether.

5. Method for the preparation of the alkaline salt of Indocyanine Green, successively comprising:

preparing the benz[e]indole of formula (V) in which, $R_1$, $R_2$, $R'_1$ and $R'_2$ are hydrogen atoms and, $R_3$, $R_4$ and $R_5$ are methyl radicals, by reaction of 2-naphthylhydrazine with isopropyl methyl ketone, reacting the benz[e]indole thus obtained with 1,4-butane-sultone, condensing the resulting product with glutaconic aldehyde dianilide hydrochloride in acetic medium, and reacting the product thus formed, in an ethanolic medium, with a molecule of the benz[e]indole of formula (I)

containing the same 1,4-butane-sultone radical on the nitrogen atom, carrying out the conversion into a water-soluble salt by directly introducing an alkaline alkoxide or an alkaline salt of an organic acid into the reaction medium.

6. Method according to claim 5, wherein the conversion into a water-soluble salt is performed by directly introducing sodium acetate into the reaction medium.

7. Substituted benz[e]indole of formula:

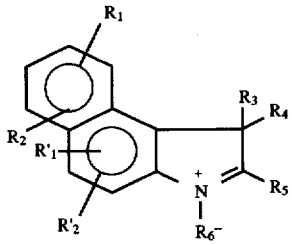

(I)

in which $R_1$, $R_2$, $R'_1$, $R'_2$, $R_3$ and $R_4$, which are identical to or different from each other, represent a hydrogen atom, a $C_1$ to $C_{12}$ alkyl group, a $C_1$ to $C_4$ sulphoalkyl, cycloalkyl or alkoxyl group, an aryl or aroxyl group, or a halogen atom, and $R_6$ represents a $C_1$ to $C_7$ sulphoalkyl, haloalkyl or hydroxycarbonylalkyl group.

$R_5$ represents a hydrogen atom, a $C_1$ to $C_{12}$ alkyl group, a $C_1$ to $C_4$ sulphoalkyl, cycloalkyl or alkoxyl group, an aryl or aroxyl group, a halogen atom or a group of formula:

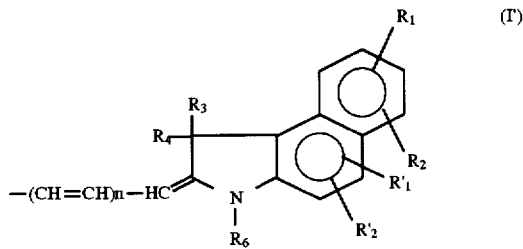

(I')

in which n represents an integrer from 1 to 7, containing less than 0.5% of residual impurities, substantially free of iodide ions and of traces of carcinogenic amines.

8. Substituted benz[e]indole according to claim 7, wherein $R_6$ represents a $C_1$ to $C_4$ sulphoalkyl, haloalkyl or hydroxycarbonylalkyl group.

9. Indocyanine Green free of iodide ions, of traces of carcinogenic amines and of toxic solvents, containing less than 0.5% of residual impurities.

* * * * *